United States Patent
Taniura

(10) Patent No.: US 10,321,981 B2
(45) Date of Patent: Jun. 18, 2019

(54) ANIMAL POSITIONER

(71) Applicants: Tokunori Taniura, Hiroshima-shi, Hiroshima (JP); PetCommunications Co., Ltd, Osaka-Shi, Osaka (JP)

(72) Inventor: Tokunori Taniura, Hiroshima (JP)

(73) Assignees: Tokunori Taniura, Hiroshima (JP); PETCOMMUNICATIONS CO., LTD., Osaka (JP)

( * ) Notice: Subject to any disclaimer, the term of this patent is extended or adjusted under 35 U.S.C. 154(b) by 128 days.

(21) Appl. No.: 15/527,442

(22) PCT Filed: Mar. 23, 2017

(86) PCT No.: PCT/JP2017/011896
§ 371 (c)(1),
(2) Date: May 17, 2017

(87) PCT Pub. No.: WO2018/016129
PCT Pub. Date: Jan. 25, 2018

(65) Prior Publication Data
US 2018/0296311 A1    Oct. 18, 2018

(30) Foreign Application Priority Data
Jul. 21, 2016 (JP) ................................ 2016-142966

(51) Int. Cl.
*A01K 15/04* (2006.01)
*A61D 3/00* (2006.01)
(Continued)

(52) U.S. Cl.
CPC .............. *A61D 3/00* (2013.01); *A01K 1/0613* (2013.01); *A01K 15/04* (2013.01); *A61B 6/032* (2013.01);
(Continued)

(58) Field of Classification Search
CPC ................ A61D 3/00; A61D 2003/003; A61D 2003/006; A61B 6/0421; A01K 15/04; A01K 1/0613
(Continued)

(56) References Cited

U.S. PATENT DOCUMENTS 2,187,337 A    1/1940  Wang
2,965,071 A *  12/1960 Scott ...................... A01K 15/00
                                                                  119/757
(Continued)

FOREIGN PATENT DOCUMENTS

CN    105361971 A    3/2016
JP    2000060879 A   2/2000
(Continued)

OTHER PUBLICATIONS

Japanese International Search Report dated Jun. 14, 2017.
Extended European Search Report dated Feb. 5, 2019.

*Primary Examiner* — Trinh T Nguyen
(74) *Attorney, Agent, or Firm* — Harness, Dickey & Pierce, P.L.C.

(57) ABSTRACT

An animal positioner includes two forelimb positioning members cylindrically attached to forelimbs of an animal, respectively, so as to wrap the forelimbs; two hindlimb positioning members cylindrically attached to hindlimbs of the animal, respectively, so as to wrap the hindlimbs, the two hindlimb positioning members being longer than the forelimb positioning members; a trunk positioning member which is longer than the hindlimb positioning members, the trunk positioning member being cylindrically attached to a trunk of the animal so as to wrap the trunk between the forelimb positioning members which are attached to the forelimbs of the animal, respectively, and the hindlimb positioning members which are attached to the hindlimbs thereof, respectively; and a head positioning member
(Continued)

attached to a head of the animal so as to form a truncated cone circumferential surface and wrap the head above the forelimb positioning members.

2 Claims, 15 Drawing Sheets

(51) Int. Cl.
*A61B 6/03* (2006.01)
*A61B 6/04* (2006.01)
*A61B 6/00* (2006.01)
*A01K 1/06* (2006.01)
*A61F 5/37* (2006.01)

(52) U.S. Cl.
CPC .......... *A61B 6/0421* (2013.01); *A61B 6/0442* (2013.01); *A61B 6/508* (2013.01); *A61F 5/3776* (2013.01); *A61D 2003/003* (2013.01); *A61D 2003/006* (2013.01)

(58) Field of Classification Search
USPC ................ 119/726, 729, 755, 756, 753, 417
See application file for complete search history.

(56) References Cited

U.S. PATENT DOCUMENTS

| | | | | |
|---|---|---|---|---|
| 4,184,451 A * | 1/1980 | Carlin | ................ | A61D 3/00 119/755 |
| 4,269,149 A | 5/1981 | Thomas | | |
| 4,459,941 A * | 7/1984 | Moffatt | ................ | A61D 3/00 119/722 |
| 4,911,106 A * | 3/1990 | Goodwin | ............... | A01K 15/00 119/724 |
| 4,934,320 A * | 6/1990 | Cresap, III | ............... | A61D 3/00 119/753 |
| 5,009,196 A * | 4/1991 | Young | ................ | A61D 3/00 119/728 |
| 5,320,069 A * | 6/1994 | Anderson, Jr. | .......... | A61D 3/00 119/751 |
| 5,383,425 A * | 1/1995 | Bleacher | ................ | A61D 3/00 119/729 |
| 5,385,119 A * | 1/1995 | Tarulli | .................... | A61D 3/00 119/755 |
| 5,823,146 A * | 10/1998 | Alaniz | ................ | A01K 15/00 119/725 |
| 5,943,983 A * | 8/1999 | Drew | ................ | A01K 1/0613 119/722 |
| 6,651,587 B1 * | 11/2003 | DeFord | ................ | A61D 3/00 119/420 |
| 7,146,936 B2 * | 12/2006 | Dazai | ................ | A61D 3/00 119/756 |
| 7,162,977 B1 * | 1/2007 | Charvat | ............... | A01K 1/0613 119/417 |
| 7,603,966 B1 * | 10/2009 | Beebe | ................ | A61D 3/00 119/755 |
| 8,051,807 B2 * | 11/2011 | Winders | ............... | A01K 1/0613 119/728 |
| 8,342,136 B2 * | 1/2013 | Hadjioannou | ........ | A61B 6/508 119/755 |
| 9,320,453 B2 * | 4/2016 | Lanz | ................ | A61B 5/0555 |
| 2003/0136354 A1 * | 7/2003 | Remmler | ................ | A61D 3/00 119/755 |
| 2008/0072836 A1 * | 3/2008 | Chiodo | ................ | A61D 3/00 119/417 |
| 2008/0308047 A1 * | 12/2008 | Mollhagen | ........... | A01K 1/0613 119/734 |
| 2011/0083614 A1 * | 4/2011 | Chen | ................ | A01K 1/0613 119/729 |
| 2011/0308478 A1 * | 12/2011 | Lee | .................. | A61D 3/00 119/752 |
| 2012/0006283 A1 * | 1/2012 | Katz | ................ | A01K 13/00 119/753 |
| 2012/0226288 A1 * | 9/2012 | Mays | ................ | A01K 11/00 606/116 |
| 2013/0213318 A1 * | 8/2013 | Katz | ................ | A01K 13/001 119/754 |

FOREIGN PATENT DOCUMENTS

| | | |
|---|---|---|
| JP | 2006230239 A | 9/2006 |
| JP | 2009034039 A | 2/2009 |

\* cited by examiner

A NIMAL POSITIONER

TECHNICAL FIELD

The present invention relates to an animal positioner which can preferably be used to position an animal, which is also referred to as a pet animal such as a dog or a cat, in a still state without anesthesia on a bed of a computed tomography (abbreviated as CT) apparatus when CT imaging of the animal as an imaging target is carried out.

BACKGROUND ART

In recent years, a computed tomography apparatus has been introduced into veterinary offices where medical care is provided to animals, which are also referred to as pet animals such as a dog and a cat, and an advanced medical examination is performed on the animals by using computed tomographic images. In the computed tomography, anesthesia is applied to restrain movement of the animal during imaging.

However, such application of anesthesia is not preferred to the animals, and a method of restraining the movement of the animal without anesthesia has been requested.

SUMMARY OF INVENTION

Technical Problem

An object of the invention is to provide an animal positioner that can restrain movement of an animal without anesthesia.

Solution to Problem

The invention provides an animal positioner, including:

two forelimb positioning members each composed of a plate-like body made of an elastically-deformable soft synthetic resin, the two forelimb positioning members being cylindrically attached to right and left forelimbs of an animal, respectively, so as to wrap the right and left forelimbs;

two hindlimb positioning members each composed of a plate-like body made of an elastically-deformable soft synthetic resin, the two hindlimb positioning members being cylindrically attached to right and left hindlimbs of the animal, respectively, so as to wrap the right and left hindlimbs, the two hindlimb positioning members being longer than the two forelimb positioning members;

a trunk positioning member composed of a plate-like body made of an elastically-deformable soft synthetic resin, the trunk positioning member being longer than the two hindlimb positioning members and being cylindrically attached to a trunk of the animal so as to wrap the trunk between the two forelimb positioning members which are attached to the right and left forelimbs of the animal, respectively, and the two hindlimb positioning members which are attached to the right and left hindlimbs thereof, respectively; and a head positioning member composed of a plate-like body made of an elastically-deformable soft synthetic resin, the head positioning member being attached to a head of the animal so as to form a truncated cone circumferential surface and wrap the head above the two forelimb positioning members.

In addition, in the invention, it is preferable that the animal positioner further includes a head retainer body made of an elastically-deformable soft synthetic resin, the head retainer body retaining the two forelimb positioning members and the head positioning member, wherein the head retainer body includes an intermediate wall section disposed between the two forelimb positioning members;

one wall section disposed on an opposite side of the intermediate wall section from one of the two forelimb positioning members in parallel with the intermediate wall section;

another wall section disposed on an opposite side of the intermediate wall section from another of the two forelimb positioning members in parallel with the intermediate wall section; and a retainer wall section fixing the intermediate wall section, the one wall section, and the other wall section in a state of being aligned in parallel so as to mount and retain thereon the head positioning member attached to the head of the animal.

Furthermore, in the invention, it is preferable that the animal positioner further includes a trunk retainer body made of an elastically-deformable soft synthetic resin, the trunk retainer body having a fitting recessed section to which the trunk positioning member cylindrically attached to the trunk of the animal can be fitted.

Advantageous Effects of Invention

According to the invention, the forelimb positioning members are cylindrically attached to the right and left forelimbs of the animal, respectively, and the hindlimb positioning members are cylindrically attached to the right and left hindlimbs of the animal, respectively. The trunk positioning member is cylindrically attached to the trunk of the animal so as to wrap the trunk, and the head positioning member is attached to the head of the animal so as to form a truncated cone circumferential surface and wrap the head.

Since the forelimb positioning members, the hindlimb positioning members, the trunk positioning member, and the head positioning member are composed of the plate-like body made of the elastically-deformable soft synthetic resin, the forelimb positioning members, the hindlimb positioning members, the trunk positioning member, and the head positioning member are wound around the forelimbs, the hindlimbs, the trunk, and the head of the animal, respectively, with appropriate strength in accordance with sizes thereof, and thus can restrain movement of the animal without applying a strong pressing force or pressurizing force to the animal. In this way, the animal can be positioned without anesthesia, and a medical examination which requires a positioned state, such as computed tomography, can be performed.

In addition, according to the invention, in the head retainer body, the one forelimb positioning member for the animal can be fitted to a space between the one wall section and the intermediate wall section, and the other forelimb positioning member for the animal can be fitted to a space between the other wall section and the intermediate wall section. Thus, movement of each of the forelimbs of the animal can further reliably be restrained. In addition, because the retainer wall section is fixed to the one wall section, the other wall section, and the intermediate wall section, the head positioning member which is attached to the head of the animal, can be mounted and retained on the retainer wall section. In this way, the head of the animal is positioned above each of the forelimbs, and a posture of the animal can be corrected to a posture which is appropriate for a medical examination purpose.

Since such a head retainer body is formed of the elastically-deformable soft synthetic resin, the head retainer body can restrain movement of the head of the animal without applying the strong pressing force or pressurizing force to the animal.

Furthermore, according to the invention, since the trunk positioning member which is cylindrically attached to the trunk of the animal, can be fitted to the fitting recessed section of the trunk retainer body, movement of the trunk of the animal can further reliably be restrained, and the posture of the animal can be corrected to a posture which is appropriate for a medical examination purpose.

BRIEF DESCRIPTION OF DRAWINGS

Other and further objects, features, and advantages of the invention will be more explicit from the following detailed description taken with reference to the drawings wherein:

FIG. 4 is a development view of the forelimb positioning member 6a;

FIG. 6 is a development view of the hindlimb positioning member 8a;

FIG. 7 is a view of a drawing tool 34 which is used to draw the forelimb 5a into the cylindrical forelimb positioning member 6a;

FIG. 9 is a view of a state where the drawing tool 34 is locked to the forelimb positioning member 6a;

DESCRIPTION OF EMBODIMENTS

Figure 1:
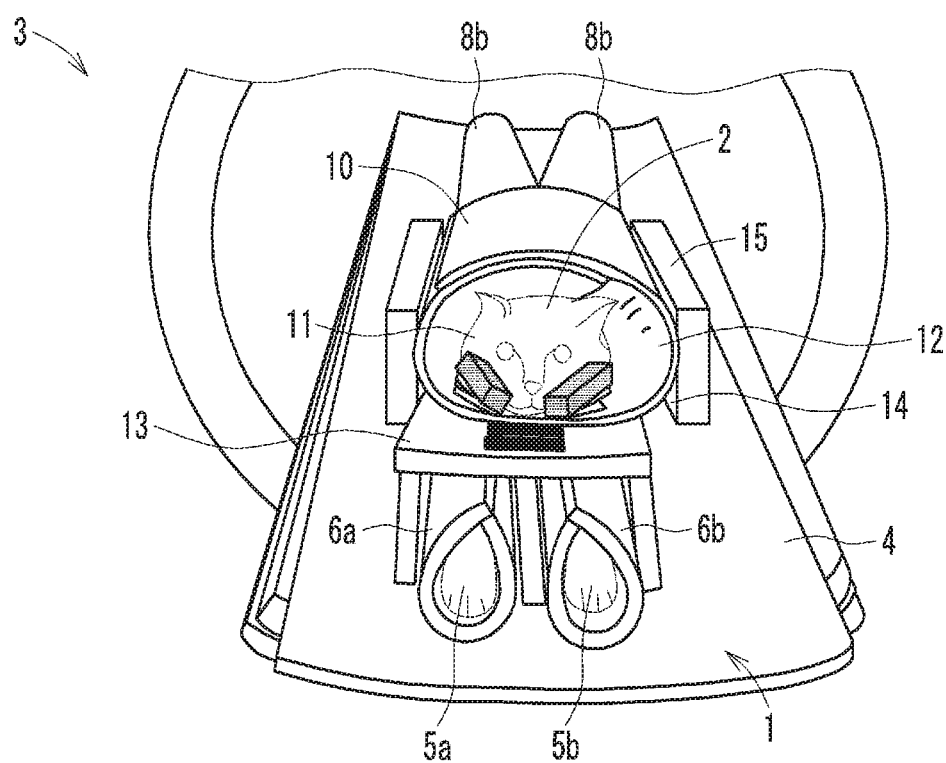
FIG. 1 is a perspective view in which a state where an animal 2, to which an animal positioner 1 of one embodiment of the invention is attached, is placed on a bed 4 of a computed tomography apparatus 3 is seen from a front side.
Figure 2:
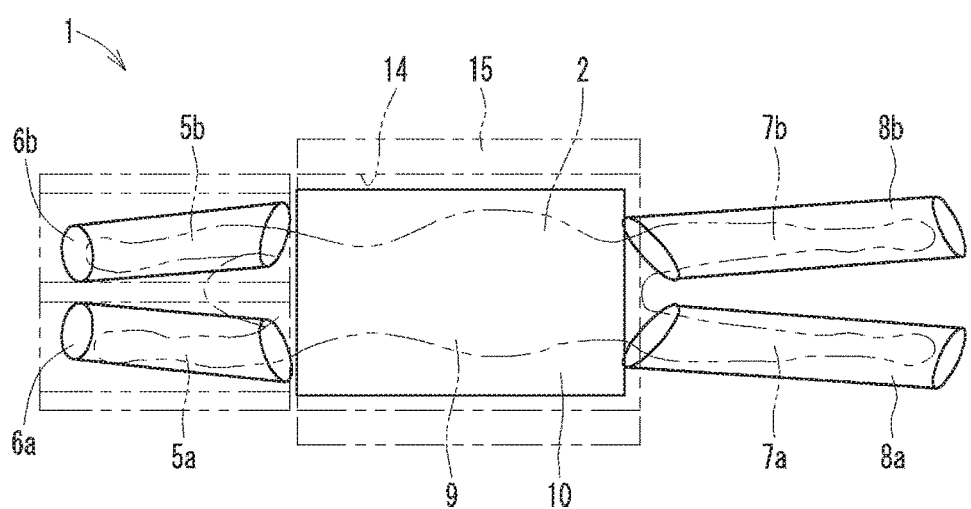
FIG. 2 is a bottom view schematically depicting an attached state of the animal positioner 1 to the animal 2.

FIG. 1 is a perspective view in which a state where an animal 2, to which an animal positioner 1 of one embodiment of the invention is attached, is placed on a bed 4 of a computed tomography apparatus 3 is seen from a front side, and FIG. 2 is a bottom view schematically depicting an attached state of the animal positioner 1 to the animal 2. In this embodiment, a case where the animal positioner 1, which is used to position the animal 2 on a bed of the computed tomography apparatus (hereinafter may be abbreviated as a "CT apparatus") without anesthesia, is attached to the animal 2 as an imaging target at a time of computed tomography (abbreviated as CT) at a veterinary office is assumed for the following description.

The animal positioner 1 of this embodiment includes: two forelimb positioning members 6a and 6b which are cylindrically attached to right and left forelimbs 5a and 5b of the animal 2, respectively, so as to wrap the forelimbs 5a and 5b; two hindlimb positioning members 8a and 8b which are cylindrically attached to right and left hindlimbs 7a and 7b of the animal 2, respectively, so as to wrap the hindlimbs 7a and 7b; a trunk positioning member 10 which is cylindrically attached to a trunk 9 of the animal 2 so as to wrap the trunk 9; a head positioning member 12 which is attached to a head 11 of the animal 2 so as to form a truncated cone circumferential surface and wrap the head 11; a head retainer body 13 which retains the two forelimb positioning members 6a and 6b and the head positioning member 12; and a trunk retainer body 14 which has a fitting recessed section to which the trunk positioning member 10, which is cylindrically attached to the trunk 9 of the animal 2, can be fitted.

In this embodiment, as described above, the animal positioner 1 includes the two forelimb positioning members 6a and 6b, the two hindlimb positioning members 8a and 8b, the trunk positioning member 10, the head positioning member 12, the head retainer body 13, and the trunk retainer body 14. However, when the movement of the animal 2 is moderate due to emaciation, or when all of those members and bodies cannot be attached due to a wound, a bone fracture, or the like, only some of the two forelimb positioning members 6a and 6b, the two hindlimb positioning members 8a and 8b, the trunk positioning member 10, the head positioning member 12, the head retainer body 13, and the trunk retainer body 14, which are described above, are appropriately selected and used for body parts where such members and/or bodies can be attached.

The two forelimb positioning members 6a and 6b, the two hindlimb positioning members 8a and 8b, the trunk positioning member 10, and the head positioning member 12, which are described above, are each composed of a plate-like body made of an elastically-deformable soft synthetic resin. In addition, the head retainer body 13 and the trunk retainer body 14 are each made of an elastically-deformable soft synthetic resin. As the elastically-deformable soft synthetic resin, a foamed synthetic resin of a closed-cell type such as a foamed urethane resin can be used. This foamed urethane resin has been confirmed by a phantom study that it has no influence on quality of images.

Figure 3:
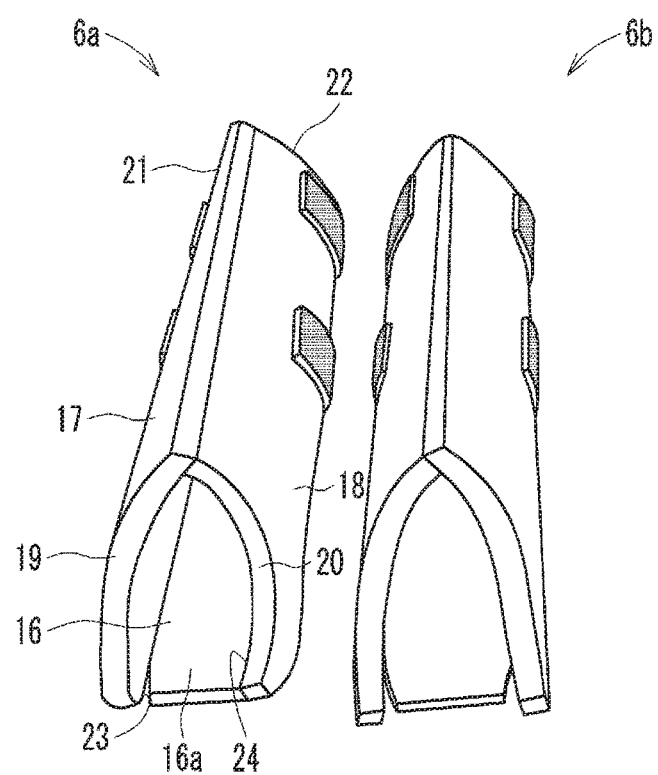
FIG. 3 is a perspective view of external appearance of cylindrical forelimb positioning members 6a and 6b.
Figure 4:
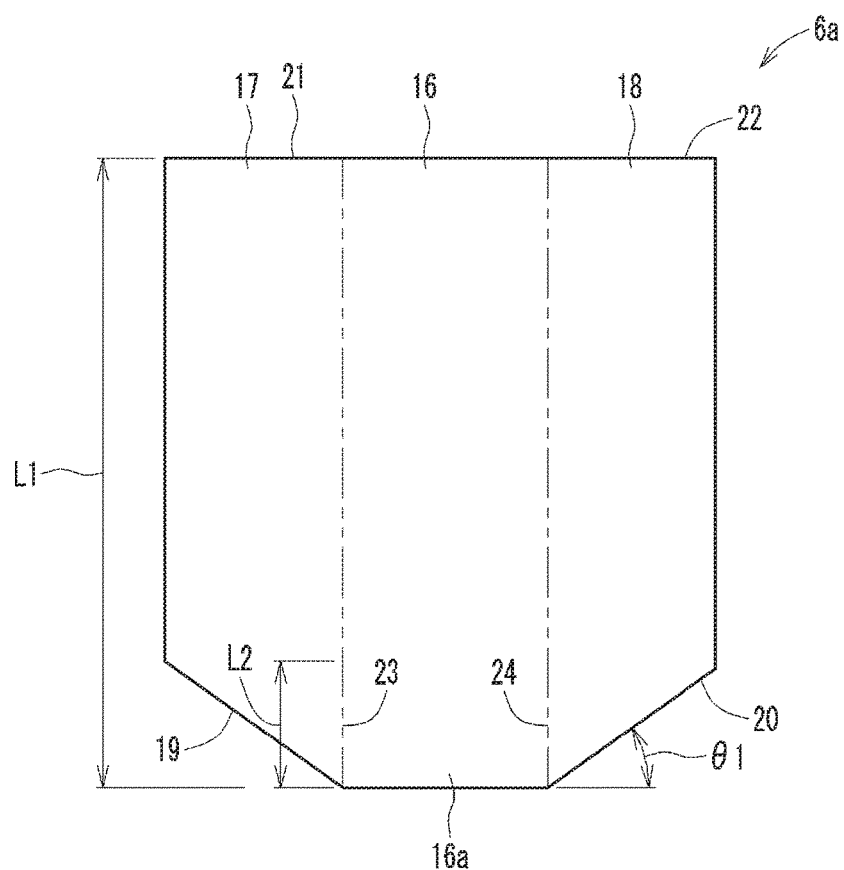

FIG. 3 is a perspective view of external appearance of the cylindrical forelimb positioning members 6a and 6b, and FIG. 4 is a development view of the forelimb positioning member 6a. Since the forelimb positioning members 6a and 6b are configured to be plane-symmetrical, only the one forelimb positioning member 6a is depicted in FIG. 4, and a description about the other forelimb positioning member 6b will be omitted to avoid an overlapping description. The one forelimb positioning member 6a has: a rectangular bottom section 16 in a state of being developed in a plane; and a pair of trapezoidal lateral sections 17 and 18 which are integrally connected to lateral ends on two long sides of the bottom section 16, respectively.

The lateral sections 17 and 18 each have: one end surfaces 19 and 20, each of which is inclined in the developed state at an angle 61 with respect to a straight line perpendicular to a long side; and other end surfaces 21 and 22, each of which is perpendicular to the long side. The angle 61 is, for example, selected from 15° to 45°.

The forelimb positioning members 6a and 6b are attached to the forelimbs 5a and 5b of the animal 2, respectively, such that the one end surfaces 19 and 20 are situated on the trunk 9 side. Since the one end surfaces 19 and 20 are inclined at the angle 61 with respect to the straight line perpendicular to the long side, one ends of the cylindrical forelimb positioning members 6a and 6b are prevented from interfering with the trunk 9 of the animal 2, and thus the forelimb positioning members 6a and 6b can be inserted to bases of the forelimbs 5a and 5b, respectively. In a state of being attached to the forelimbs 5a and 5b of the animal 2, the forelimb positioning members 6a and 6b cover from bases of humeri to tips of toes, and flexing actions at joints of the forelimbs 5a and 5b are thereby restrained.

At one longitudinal ends of the forelimb positioning members 6a and 6b, notches 23 and 24, which longitudinally extend by a length L2 from the one longitudinal end to the other longitudinal end, are formed between the bottom section 16 and the one lateral section 17 and between the bottom section 16 and the other lateral section 18, respectively. By such notches 23 and 24, a portion 16a of the bottom section 16 between the notches 23 and 24 can be freed from restraint by the lateral sections 17 and 18 on both sides thereof and can thereby follow movement of the forelimbs 5a and 5b. The length L1 of the forelimb positioning member 6a is selected to a length which is substantially equal to length of the forelimb 5a in a stretched state.

Figure 5:
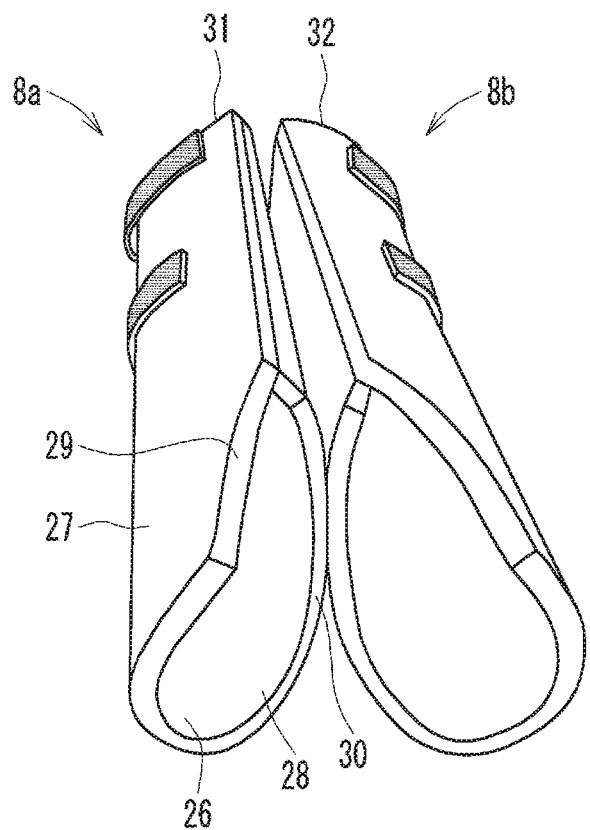
FIG. 5 is a perspective view of external appearance of cylindrical hindlimb positioning members 8a and 8b.
Figure 6:
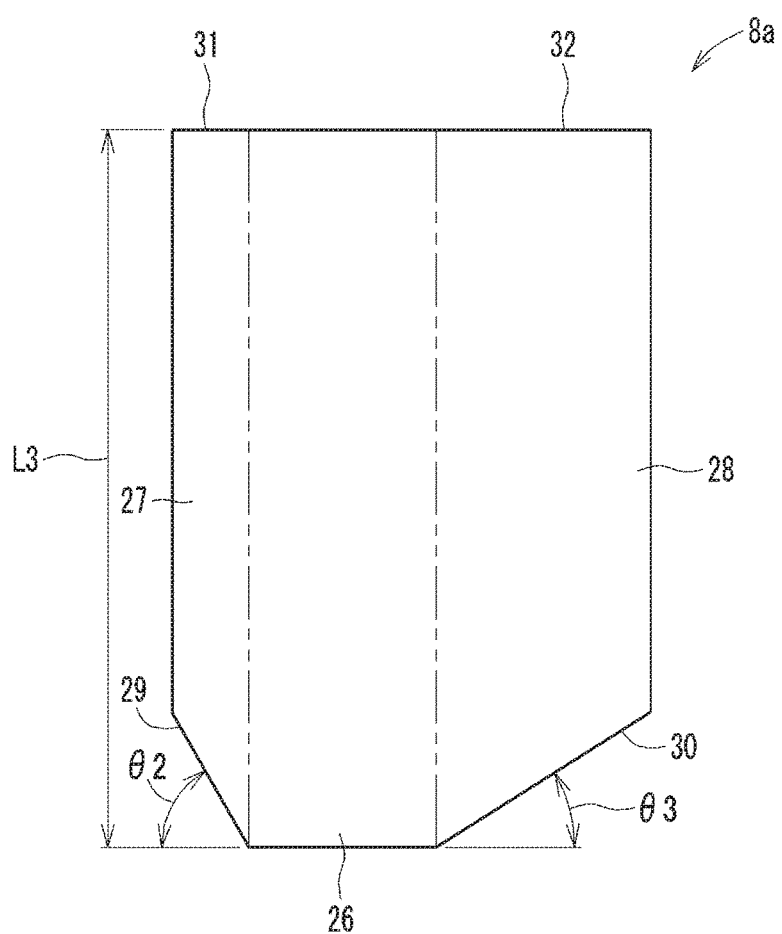

FIG. 5 is a perspective view of external appearance of the cylindrical hindlimb positioning members 8a and 8b, and FIG. 6 is a development view of the hindlimb positioning member 8a. Since the two hindlimb positioning members 8a and 8b are configured to be plane-symmetrical, only the one hindlimb positioning member 8a is depicted in FIG. 6, and a description about the other hindlimb positioning member 8b will be omitted to avoid an overlapping description. The one hindlimb positioning member 8a has: a rectangular bottom section 26 in a state of being developed in a plane; a trapezoidal lateral section 27 which is connected to a lateral end on one long side of the bottom section 26; and a trapezoidal lateral section 28 which is connected to the other lateral end of the bottom section 26.

The lateral sections 27 and 28 each have: one end surfaces 29 and 30 which are inclined in the developed state at angles 62 and 63 with respect to a straight line perpendicular to the long side, respectively; and other end surfaces 31 and 32, each of which is perpendicular to the long side. The angles 62 and 63 are, for example, selected from 15° to 45°. A longitudinal length L3 of the hindlimb positioning member 8a is selected to length that is longer than the length L1 of the above-described forelimb positioning member 6a and that is substantially equal to length of the hindlimb 7a in a stretched state.

The hindlimb positioning members 8a and 8b are attached to the hindlimbs 7a and 7b of the animal 2, respectively, such that the one end surfaces 29 and 30 are situated on the trunk 9 side. Since the one end surfaces 29 and 30 are inclined at the angles 62 and 63 with respect to the straight line which is perpendicular to the long side, respectively, portions at one ends of the cylindrical hindlimb positioning members 8a and 8b are prevented from interfering with the trunk 9 of the animal 2, and thus the hindlimb positioning members 8a and 8b can be inserted to bases of the hindlimbs 7a and 7b, respectively. In a state of being attached to the hindlimbs 7a and 7b of the animal 2, the hindlimb positioning members 8a and 8b cover from bases of femora to tips of toes, and flexing actions at joints of the hindlimbs 7a and 7b are thereby restrained.

Figure 7:
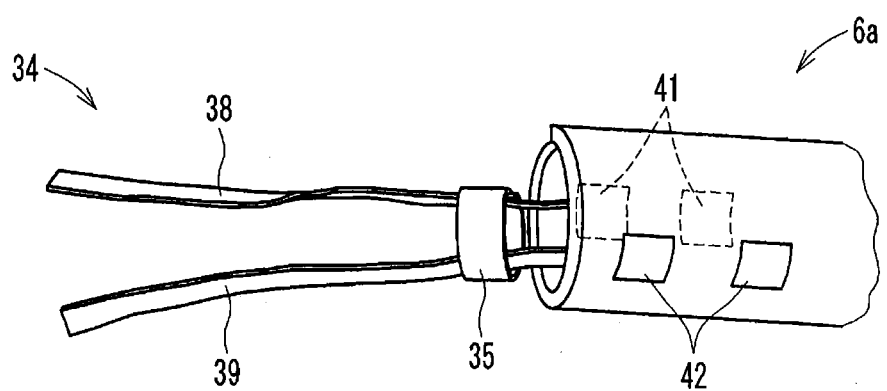
Figure 8:
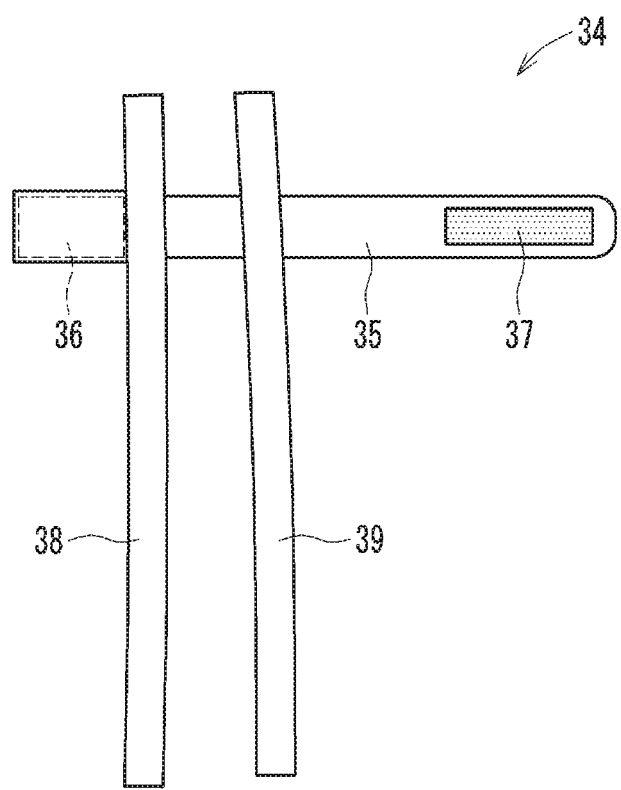
FIG. 8 is a development view of the drawing tool 34.
Figure 9:
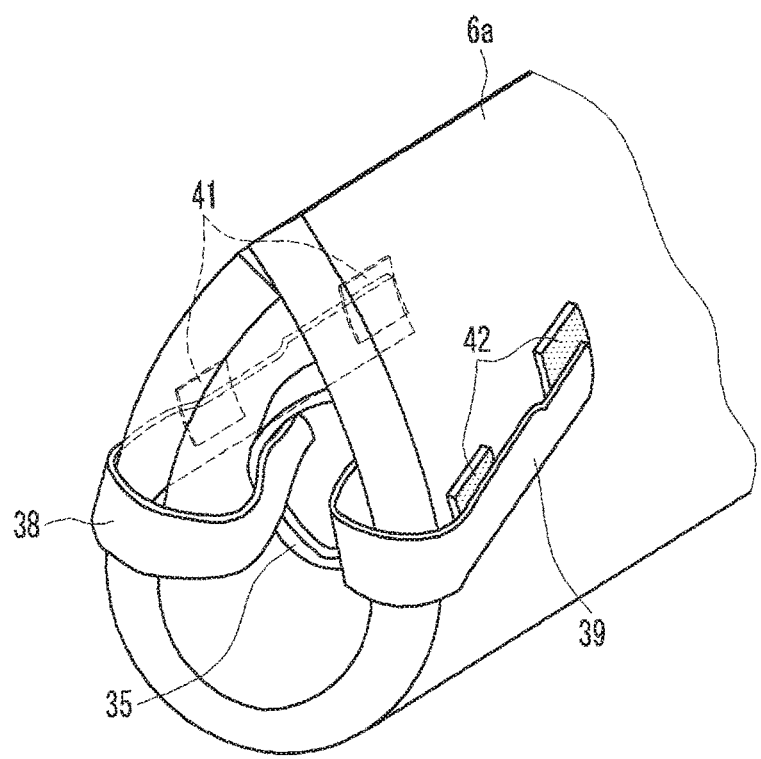

FIG. 7 is a view of a drawing tool 34 which is used to draw the forelimb 5a into the cylindrical forelimb positioning member 6a, FIG. 8 is a development view of the drawing tool 34, and FIG. 9 is a view of a state where the drawing tool 34 is locked to the forelimb positioning member 6a. Note that the drawing tool 34 can be used in a similar manner for the other forelimb positioning member 6b and each of the hindlimb positioning members 8a and 8b, and thus, as one aspect, the drawing tool 34 used for the one forelimb positioning member 6a will be described.

The drawing tool 34 is used to maintain the forelimb 5a of the animal 2 in a drawn and stretched state in the cylindrical forelimb positioning member 6a. The drawing tool 34 includes: a first belt-like member 35 which is wound around the forelimb 5a of the animal 2; a first fastener piece 36 which is joined to one surface section at one longitudinal end of the first belt-like member 35 by adhesion or sewing; a second fastener piece 37 which is joined to another surface section at another longitudinal end of the first belt-like member 35 by adhesion or sewing; a narrow-width second belt-like member 38 which is joined to the other surface section of a portion near one end in an intermediate section between both of the longitudinal ends of the first belt-like member 35 by adhesion or sewing; and a narrow-width third belt-like member 39 which is joined to the other surface section of a portion near the second belt-like member 38 in the intermediate section between both of the longitudinal ends of the first belt-like member 35 by adhesion or sewing.

The first fastener piece 36, the second fastener piece 37, the second belt-like member 38, and the third belt-like member 39 are each realized by a hook-and-loop fastener which is also referred to as a Velcro tape or a fastener tape. The first fastener piece 36 and the second fastener piece 37 can removably be attached to each other. The first belt-like member 35 is wound around the forelimb 5a of the animal 2, the first fastener piece 36 and the second fastener piece 37 are attached to each other at an appropriate fastening position, and thereby the drawing tool 34 can be attached to the forelimb 5a.

The lateral sections 17 and 18 of the forelimb positioning member 6a are provided with a third fastener piece 41 and a fourth fastener piece 42, respectively. The third fastener piece 41 and the second belt-like member 38 can be removably attached to each other. In addition, the fourth fastener piece 42 and the third belt-like member 39 can be removably attached to each other. After the first belt-like member 35 is wound around the forelimb 5a as described above and the drawing tool 34 is thereby attached thereto in the developed state of the forelimb positioning member 6a, the second and third belt-like members 38 and 39 are drawn to appropriate drawing positions and are then attached to the third and fourth fastener pieces 41 and 42, respectively, as depicted in FIG. 9. In this way, the forelimb positioning member 6a is attached to the forelimb 5a in the stretched state of the forelimb 5a, and the movement of the forelimb 5a can thereby be restrained.

In regard to the other forelimb positioning member 6b and each of the hindlimb positioning members 8a and 8b, by using the drawing tool 34 in a similar configuration, the other forelimb positioning member 6b and the hindlimb positioning members 8a and 8b are attached to the other forelimb 5b and the hindlimbs 7a and 7b, respectively, and movement of the other forelimb 5b and the hindlimbs 7a, 7b can thereby be restrained.

In order to prevent opening of each of the forelimb positioning members 6a and 6b, each of the hindlimb positioning members 8a and 8b, and the trunk positioning member 10, which have been described above, from a cylindrically curved state due to resilience of itself or the movement of the animal 2, a belt-like flexible fixing member is adhered over both ends thereof that oppose each other or adjacently overlap each other in the cylindrically curved state so as to allow separation of both of the ends from each other. Such a fixing member may be, for example, the above-described belt-like hook-and-loop fastener or an adhesive tape.

Figure 10:
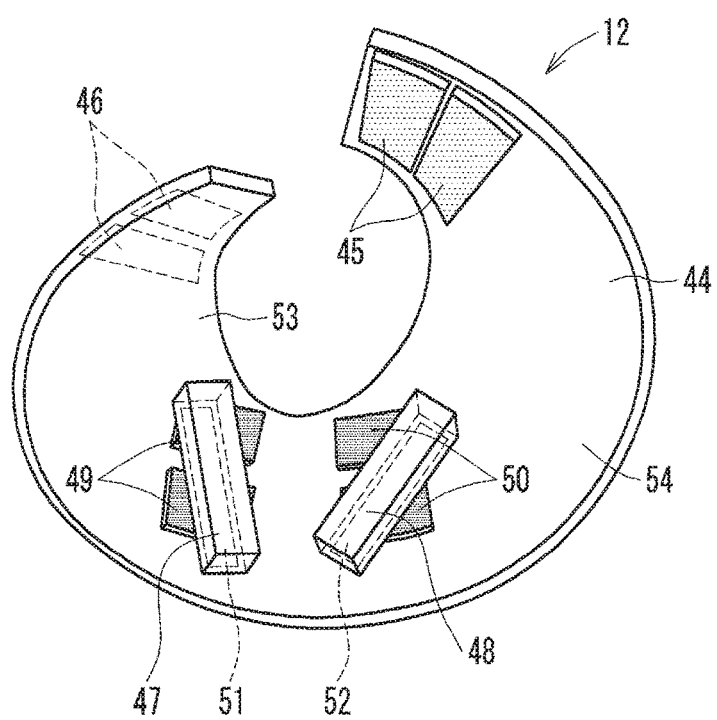
FIG. 10 is a perspective view of a head positioning member 12.

FIG. 10 is a perspective view of the head positioning member 12. The head positioning member 12 is composed of a plate-like body made of the elastically-deformable soft synthetic resin, and has: a substantially fan-shaped cover body 44 in a state of being developed in a plane; a first fastener piece 45 which is joined to an inner surface at one end of the cover body 44 in a circumferential direction (that is, a longitudinal direction in the developed state) by adhesion or sewing; and a second fastener piece 46 which is joined to an outer surface at another end of the cover body 44 in the circumferential direction by adhesion or sewing.

In this embodiment, in order to position the head 11 of the animal 2, two pad members 47 and 48 are provided in the vicinity of each other on both sides of a circumferentially central section of the cover body 44. These pad members 47 and 48 are each composed of a rectangular parallelepiped block having a small thickness, and the third and fourth fastener pieces 49 and 50 are joined to one surfaces thereof in a thickness direction by adhesion. Fifth and sixth fastener pieces 51 and 52 are joined to an inner surface at both of the ends of the circumferentially central section of the cover body 44 by adhesion or sewing. These third to sixth fastener pieces 49 to 52 are each composed of a hook-and-loop fastener similar to the above. The third fastener piece 49 and the fifth fastener piece 51 are removable, and the fourth fastener piece 50 and the sixth fastener piece 52 are removable.

In a state where the first fastener piece 45 and the second fastener piece 46 overlap and are joined to each other, the cover body 44 includes a cylindrical body having the truncated cone circumferential surface and is configured as a truncated cone shape, that is, a so-called megaphone shape having a small-diameter opening 53 which surrounds a cervix of the animal 2; and a large-diameter opening 54 which has a larger diameter than the small-diameter opening 53, and the movement of the head 11 can be restrained by the cover body 44. Here, the truncated cone shape means a shape in which a cross-sectional area decrease (or increase) with movement in an axial direction thereof, and includes a configuration which is divided in the circumferential direction.

Figure 11:
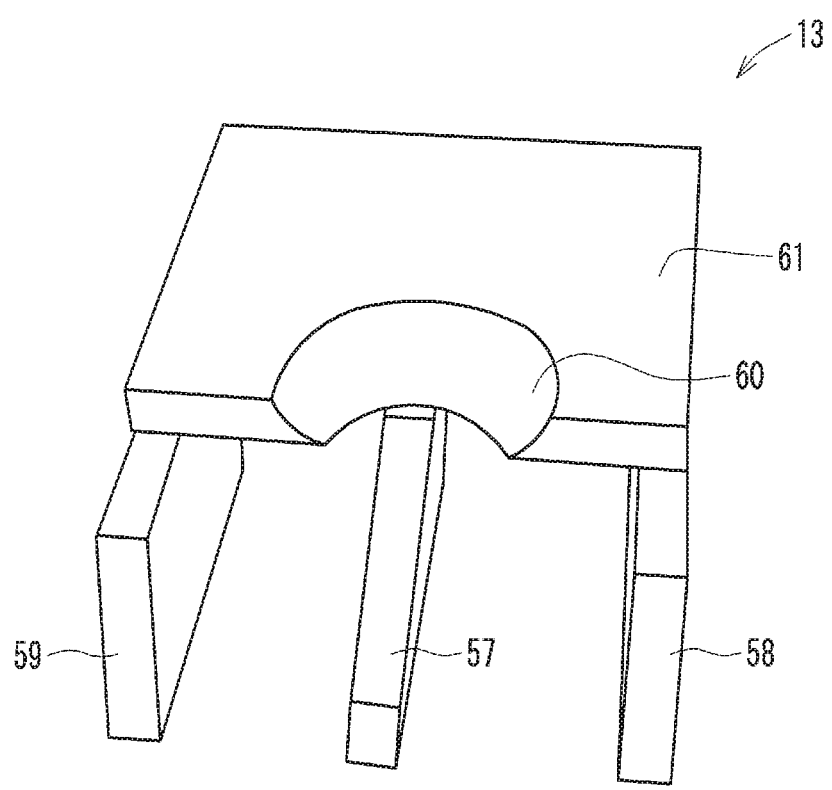
FIG. 11 is a perspective view of a head retainer body 13.
Figure 12:
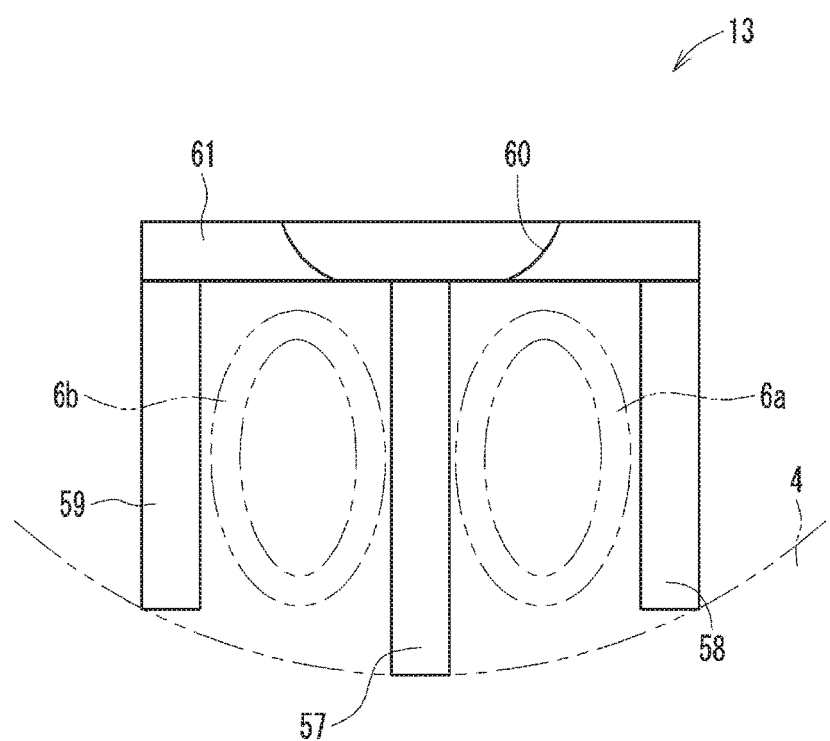
FIG. 12 is a front view of the head retainer body 13.
Figure 13:
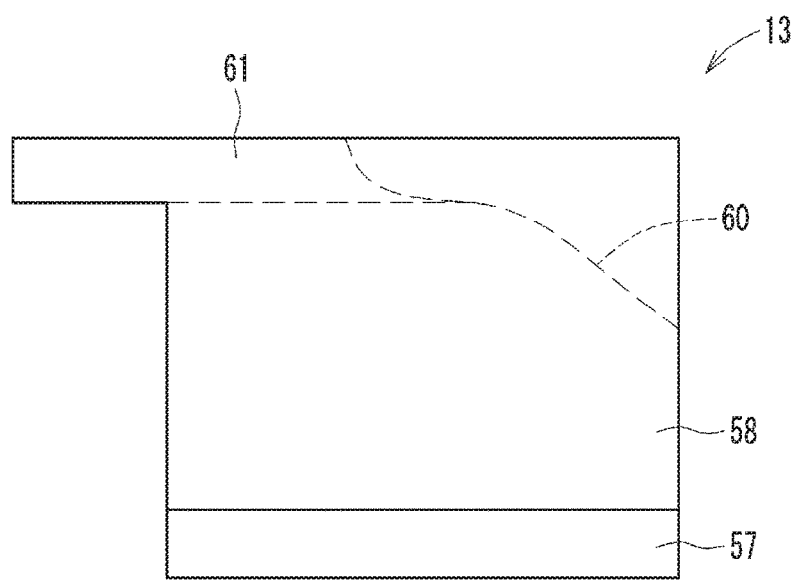
FIG. 13 is a left view of the head retainer body 13.

FIG. 11 is a perspective view of the head retainer body 13, FIG. 12 is a front view of the head retainer body 13, and FIG. 13 is a left view of the head retainer body 13. The head retainer body 13 of this embodiment has: an intermediate wall section 57 disposed between the two forelimb positioning members 6a and 6b; one wall section 58 which is disposed on an opposite side of the intermediate wall section 57 from the one forelimb positioning member 6a in parallel with the intermediate wall section 57; another wall section 59 which is disposed on an opposite side of the intermediate wall section 57 from the other forelimb positioning member 6b in parallel with the intermediate wall section 57; and a retainer wall section 61 fixing the intermediate wall section 57, the one wall section 58, and the other wall section 59 in a state of being aligned in parallel, the retainer wall section 61 having a positioning recessed section 60 constituting a part of a truncated cone the retainer wall section 61 mounting and retaining thereon the head positioning member 12 attached to the head 11 of the animal 2. Such a head retainer body 13 may be realized by an integrally molded member made of the elastically-deformable soft synthetic resin such as a foamed urethane resin.

Figure 14:
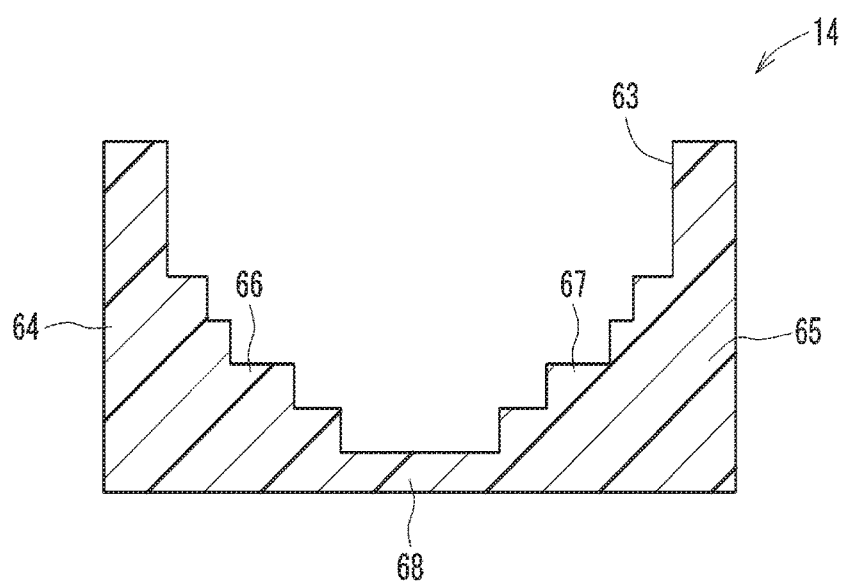
FIG. 14 is a cross-sectional view of a trunk retainer body 14.
Figure 15:
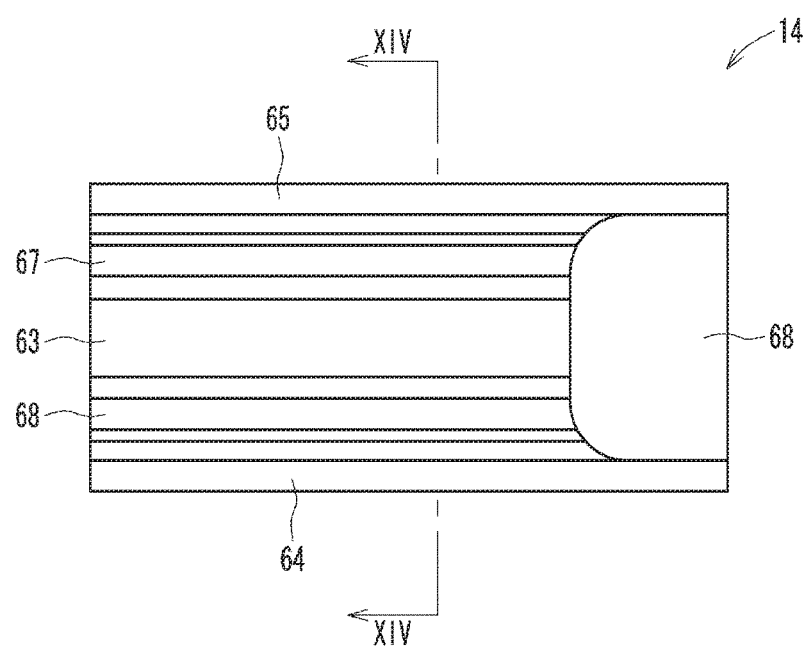
FIG. 15 is a plan view of the trunk retainer body 14.

FIG. 14 is a cross-sectional view of the trunk retainer body 14, and FIG. 15 is a plan view of the trunk retainer body 14. FIG. 14 depicts a cross section taken along the line XIV-XIV in FIG. 15. The trunk retainer body 14 of this embodiment is made of the elastically-deformable soft synthetic resin and is composed of a molded body with a recessed cross section having a fitting recessed section 63 to which the trunk positioning member 10, which is cylindrically attached to the trunk 9 of the animal 2 in the cylindrical shape, can be fitted. The trunk retainer body 14 has a pair of lateral wall sections 64 and 65; a pair of inclined sections 66 and 67 which are inclined downward in a stepwise manner in a direction to approach each other from opposing inner surfaces of the lateral wall sections 64 and 65, respectively; and a plate-shaped bottom section 68 which is connected to a bottom surface of each of the lateral wall sections 64 and 65 and a bottom surface of each of the inclined sections 66 and 67. Such a trunk retainer body 14 may be realized by an integrally molded member made of the elastically-deformable soft synthetic resin such as a foamed urethane resin.

According to this embodiment, the forelimb positioning members 6a and 6b are cylindrically and attached to the right and left forelimbs 5a and 5b of the animal 2, respectively, and the hindlimb positioning members 8a and 8b in the cylindrical shapes are attached to the right and left hindlimbs 7a and 7b of the animal 2, respectively. The trunk positioning member 10 is cylindrically attached to the trunk 9 of the animal 2 so as to wrap the trunk 9, and the head positioning member 12 is attached to the head 11 of the animal 2 so as to form a truncated cone circumferential surface.

Since the forelimb positioning members 6a and 6b, the hindlimb positioning members 8a and 8b, the trunk positioning member 10, and the head positioning member 12 are composed of the plate-like body made of the elastically-deformable soft synthetic resin, the forelimb positioning members 6a and 6b, the hindlimb positioning members 8a and 8b, the trunk positioning member 10, and the head positioning member 12 are wound around the forelimbs 5a and 5b, the hindlimbs 7a and 7b, the trunk 9, and the head 11 of the animal 2, respectively, with appropriate strength in accordance with sizes thereof, and thus can restrain the movement of the animal 2 without applying a strong pressing force or pressurizing force to the animal 2. In this way, the animal 2 can be positioned without anesthesia, and a medical examination that requires a positioned state, such as computed tomography, can be performed.

In the head retainer body 13, the one forelimb positioning member 6a of the animal 2 can be fitted to one space between the one wall section 58 and the intermediate wall section 57, and the other forelimb positioning member 6b of the animal 2 can be fitted to another space between the other wall section 59 and the intermediate wall section 57. Thus, the movement of each of the forelimbs 5a and 5b of the animal 2 can further reliably be restrained. In addition, since the retainer wall section 61 is fixed to the one wall section 58, the other wall section 59 and the intermediate wall section 57, the head positioning member 12 which is attached to the head 11 of the animal 2, can be mounted, positioned, and retained on the positioning recessed section 60 of the retainer wall section 61. In this way, the head 11 of the animal 2 is positioned above each of the forelimbs 5a and 5b, and a posture of the animal 2 can be corrected to a posture which is appropriate for the tomography, for example.

Since such a head retainer body 13 is made of the elastically-deformable soft synthetic resin, the head retainer body 13 can restrain the movement of the head 11 of the animal 2 without applying the strong pressing force or pressurizing force to the animal 2.

In addition, according to this embodiment, since the trunk positioning member 10 which is cylindrically attached to the trunk 9 of the animal 2, can be fitted to the fitting recessed section 63 of the trunk retainer body 14, the movement of the trunk 9 of the animal 2 can further reliably be restrained, and the posture of the animal 2 can be corrected to a posture which is appropriate for a medical examination purpose such as tomography.

In the above-described embodiment, the case where the animal 2 is the cat has been described. However, the invention is not limited thereto, and the animal positioner of the invention can preferably be implemented for other animals, for example, various types of animals as targets of the medical examination, such as a small dog, a middle-sized dog, and a rabbit, and can be used in various applications such as testing, measurement, diagnosis, and medical treatment.

The animal positioner of the invention is not limited to the above-described foamed urethane resin, but any of various elastically-deformable soft synthetic resins can be used as long as it is confirmed by the phantom test that the quality of the images is not degraded.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

REFERENCE SIGNS LIST

1: Animal positioner
2: Animal
3: Computed tomography apparatus
4: Bed
5a, 5b: Forelimb
6a, 6b: Forelimb positioning member
7a, 7b: Hindlimb
8a, 8b: Hindlimb positioning member
9: Trunk
10: Trunk positioning member
11: Head
12: Head positioning member
13: Head retainer body
14: Trunk retainer body
23, 24: Notch
57: Intermediate wall section
58: One wall section
59: Another wall section
60: Positioning recessed section
61: Retainer wall section
63: Fitting recessed section

The invention claimed is:

1. An animal positioner, comprising:
two forelimb positioning members each composed of a plate-like body made of an elastically-deformable soft synthetic resin, the two forelimb positioning members being cylindrically attached to right and left forelimbs of an animal, respectively, so as to wrap the right and left forelimbs;
two hindlimb positioning members each composed of a plate-like body made of an elastically-deformable soft synthetic resin, the two hindlimb positioning members being cylindrically attached to right and left hindlimbs of the animal, respectively, so as to wrap the right and left hindlimbs, the two hindlimb positioning members being longer than the two forelimb positioning members;
a trunk positioning member composed of a plate-like body made of an elastically-deformable soft synthetic resin, the trunk positioning member being longer than the two hindlimb positioning members and being cylindrically attached to a trunk of the animal so as to wrap the trunk between the two forelimb positioning members which are attached to the right and left forelimbs of the animal, respectively, and the two hindlimb positioning members which are attached to the right and left hindlimbs thereof, respectively;
a head positioning member composed of a plate-like body made of an elastically-deformable soft synthetic resin, the head positioning member being attached to a head of the animal so as to form a truncated cone circumferential surface and wrap the head above the two forelimb positioning members; and a head retainer body made of an elastically-deformable soft synthetic resin, the head retainer body retaining the two forelimb positioning members and the head positioning member, wherein the head retainer body includes an intermediate wall section disposed between the two forelimb positioning members, one wall section disposed on an opposite side of the intermediate wall section from one or the two forelimb positioning members in parallel with the intermediate wall section, another wall section disposed on an opposite side of the intermediate wall section from another of the two forelimb positioning members in parallel with the intermediate wall section, the one wall section, and the other wall section in a state of being aligned in parallel so as to mount and retain the head positioning member attached to the head of the animal thereon.

2. The animal positioner according to claim 1, further comprising a trunk retainer body made of an elastically-deformable soft synthetic resin, the trunk retainer body having a fitting recessed section to which the trunk positioning member cylindrically attached to the trunk of the animal can be fitted.

* * * * *